United States Patent
Zhong et al.

(10) Patent No.: US 8,722,074 B2
(45) Date of Patent: May 13, 2014

(54) MEDICAL DEVICES CONTAINING RADIATION RESISTANT POLYMERS

(75) Inventors: Sheng-Ping Zhong, Shrewsbury, MA (US); Enxin Ma, Framingham, MA (US); Eun-Hyun Jang, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1960 days.

(21) Appl. No.: 11/184,196

(22) Filed: Jul. 19, 2005

(65) Prior Publication Data
US 2007/0020307 A1    Jan. 25, 2007

(51) Int. Cl.
*A61F 2/02*    (2006.01)

(52) U.S. Cl.
USPC ........................................... 424/423

(58) Field of Classification Search
CPC ........................................ A61L 31/10
USPC ........................................... 424/423
See application file for complete search history.

(56) References Cited

U.S. PATENT DOCUMENTS

| | | | | |
|---|---|---|---|---|
| 4,521,570 A | * | 6/1985 | Watanabe et al. | 525/415 |
| 5,112,887 A | | 5/1992 | Colon et al. | 523/400 |
| 5,118,726 A | | 6/1992 | Mizutani et al. | 523/136 |
| 5,496,886 A | | 3/1996 | Courlias | 524/540 |
| 6,034,160 A | | 3/2000 | Eaton et al. | 524/376 |
| 6,235,842 B1 | | 5/2001 | Kuwano et al. | 525/119 |
| 7,001,421 B2 | * | 2/2006 | Cheng et al. | 623/1.11 |
| 7,144,419 B2 | * | 12/2006 | Cheng et al. | 623/1.11 |
| 2002/0111590 A1 | * | 8/2002 | Davila et al. | 604/265 |
| 2004/0162609 A1 | * | 8/2004 | Hossainy et al. | 623/1.42 |
| 2005/0148738 A1 | * | 7/2005 | Leon et al. | 525/386 |

FOREIGN PATENT DOCUMENTS

| DE | 10021605 | | 11/2001 | | A61K 6/00 |
|---|---|---|---|---|---|
| EP | 1440700 | * | 7/2004 | | A61L 31/10 |
| WO | WO 01/49327 A2 | | 7/2001 | | |
| WO | WO 2005/014745 A1 | | 2/2005 | ........... | C09D 201/00 |
| WO | WO 2007/003516 A2 | | 1/2007 | | |

OTHER PUBLICATIONS

10th edition of the Merriam-Webster's Collegiate Dictionary (Merriam-Webster Incorporated: Springfield, Massachusetts, 1993, pp. 311).*
Wikipidea (http://en.wikipedia.org/wiki/Epoxy (retrieved on Jun. 28, 2007).*
Hemmerich (Polymer materials selection for radiation sterilized products. Medical Device and Diagnostic Industry. p. 78-89 (Feb. 2002).*
InChem phenoxy brochure (http://www.brenntagspecialties.com/en/downloads/Products/ACES/InChem/InChem_Phenoxy_Brochure.pdf (downloaded on Apr. 20, 2013)).*
W.E. Skiens et al., "Ionizing Radiation's Effects on Selected Biomedical Polymers," in *Biocompatible Polymers, Metals, and Composites*, ed. M. Szycher, Society of Plastic Engineers, 1983, chap. 44, pp. 1001-1018.
Product Safety Assessment, Bisphenol A Diglycidyl Ether. http://www.dow.com/PublishedLiterature/dh_0585/09002f13805856d3.pdf?filepath=productsafety/pdfs/noreg/233-00241.pdf&fromPage=GetDoc. Jun. 24, 2004, 5 pgs.
Epoxy. http://en.wikipedia.org/wiki/Epoxy. (retrieved on May 24, 2007), but before date of instant application, 5 pgs.
Karl J. Hemmerich, "Polymer Materials Selection for Radiation-Sterilized Products," *Medical Device & Diagnostic Industry*, Feb. 2000, pp. 78-89.
Hideharu Shintani, "Study on Radiation Sterilization-Resistant Polysulfones Fabricated Free from Bisphenol A," *Trends Biomater. Artif. Organs*, vol. 18, Jul. 2000, pp. 36-40.

* cited by examiner

*Primary Examiner* — Jake Vu
(74) *Attorney, Agent, or Firm* — Fish & Richardson P.C.

(57) ABSTRACT

The present invention relates generally to radiation-resistant medical devices which contain polymer regions for release of therapeutic agents. The present invention also relates to radiation-resistant copolymer materials for use in connection with insertable or implantable medical devices. The radiation-sterilized medical device comprises (a) a release region and (b) at least one therapeutic agent and the release region comprises a phenoxy resin block.

20 Claims, 1 Drawing Sheet

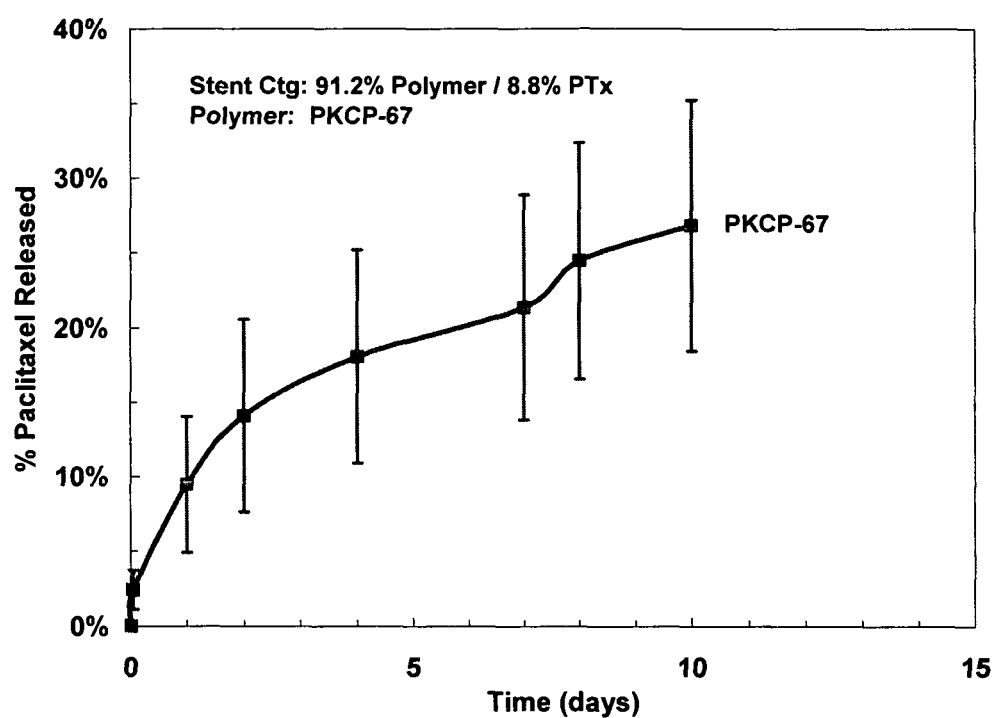

MEDICAL DEVICES CONTAINING RADIATION RESISTANT POLYMERS

FIELD OF THE INVENTION

The present invention relates generally to medical devices which contain polymer containing regions for release of therapeutic agents. The present invention also relates to radiation resistant block copolymer compositions containing biodisintegrable materials for use in connection with insertable or implantable medical devices.

BACKGROUND OF THE INVENTION

Numerous polymer-based medical devices have been developed for the delivery of therapeutic agents to the body. In accordance with some typical delivery strategies, a therapeutic agent is provided within a polymeric carrier layer and/or beneath a polymeric barrier layer that is associated with a medical device. Once the medical device is placed at the desired location within a patient, the therapeutic agent is released from the medical device at a rate that is dependent upon the nature of the polymeric carrier and/or barrier layer.

Materials which are suitable for use in making implantable or insertable medical devices typically exhibit one or more of the qualities of exceptional biocompatibility, extrudability, elasticity, moldability, good fiber forming properties, tensile strength, durability, and the like. Moreover, the physical and chemical characteristics of the device materials can play an important role in determining the final release rate of the therapeutic agent.

Phenoxy resins comprise a family of polymers that possess many properties that make them good candidates for use in drug delivery applications. These linear thermoplastic resins of high molecular weight are tough, ductile, amorphous polymers having excellent thermal stability and radiation resistance, adhesive and cohesive strength, and excellent vapor barrier properties. The backbone ether linkages and pendant hydroxyl groups promote wetting and bonding with substrate surfaces. These backbone hydroxyl groups also react with crosslinking groups like isocyanates, phenolic and melamine resins. Further, modification by esterification of the backbone hydroxyl groups which introduces pendant primary hydroxyl groups has been found to produce high molecular weight resins of vastly improved elasticity and permeability.

Materials incorporated into a finished medical device typically undergo a sterilization process. Radiation sterilization, whether by gamma rays, X-rays, accelerated electrons, or other means, is a widely-used method for sterilizing medical devices. Products to be sterilized are typically exposed to gamma rays from a Co-60 or a Cs-137 source or to machine accelerated electrons until the desired dose is received. No toxic agents are involved, and products may be released for sale on the basis of documentation that the desired dose is delivered. For the sterilization of polymeric medical devices, a typical radiation dose of about 1.0-5.0 Mrad (10-50 kGy) or higher, is employed.

Radiation sterilization, however, may modify many important physical and chemical properties of polymeric materials such as the molecular weight, chain length, entanglement, polydispersity, branching, pendant functionality, and chain termination. These changes in the properties may impair the performance of a polymer for a specific use. For example, from a product use standpoint, mechanical properties are important characteristics that may be adversely affected by irradiation of polymers. These properties include tensile strength, elastic modulus, impact strength, shear strength, and elongation. As another example, the drug-eluting properties of a drug eluting stent may be adversely impacted.

For polymers with carbon-carbon backbones, it has been observed that cross-linking generally will occur if the carbons have one or more hydrogen atoms attached, whereas chain-scission generally occurs at tetra-substituted carbons. Polymers containing aromatic molecules, such as phenoxy resins, are generally more resistant to radiation degradation than are aliphatic polymers; this is true whether or not the aromatic group is directly in the chain backbone or not. Thus, both polystyrenes, with a pendant aromatic group, and polyimides and phenoxy resins, with an aromatic group directly in the polymer backbone, are relatively resistant to high doses (>4000 kGy). A summary of the effects of radiation on polymer properties, such as loss of elongation, for a number of common thermoplastics and thermosets is provided in "Polymer Materials Selection for Radiation-Sterilized Products" by Karl J. Hemmerich, *Medical Device & Diagnostic Industry Magazine*, February 2000, pp. 78-89, the entire contents of which are hereby incorporated by reference.

However, many drug delivery polymers, for example, homopolymers and copolymers containing polyisobutylene, such as a polystyrene-polyisobutylene-polystyrene triblock copolymers, are generally more susceptible to radiation effects and may undergo chain scission during irradiation, especially at the radiation levels typically used for medical device sterilization (e.g., about 2.5 Mrad). Radiation issues are particularly pronounced in medical devices having thin polymer coatings such as the thin coating on the surface of an expandable medical device such as a stent or balloon. Radiation can lead to an unacceptable increase in the surface tack of the coating, which can in turn cause defects in the polymer when it is expanded (e.g., in situations where it is in the form of a coating on the surface of an expandable stent or balloon).

Hence, it would be advantageous to provide polymers that have a variety of desirable properties (e.g., drug release characteristics and biostability/biocompatibility) but which also exhibit improved immunity to radiation-based changes in polymer properties.

SUMMARY OF THE INVENTION

These and other challenges are addressed by the present invention which provides a radiation resistant medical device that contains (a) at least one release region that contains or consists essentially of a radiation resistant polymer and (b) at least one therapeutic agent. The radiation resistant polymer, in turn, contains or consists essentially of one or more phenoxy resin blocks.

The present invention is advantageous in that a medical device can be provided, which in addition to being resistant to the damaging effects of radiation sterilization has desirable mechanical characteristics and a desired drug release profile for providing a therapeutic agent. In addition, the present invention provides devices wherein the biodisintegrable and biostable characteristics of the device can be fabricated to suit a variety of medical needs.

These and other embodiments and advantages of the present invention will become immediately apparent to those of ordinary skill in the art upon review of the Detailed Description and Claims to follow.

BRIEF DESCRIPTION OF THE DRAWING

FIG. 1 graphically illustrates the kinetic release rate of the therapeutic agent, paclitaxel, as a function of time for stents coated with a polymer made of caprolactone-modified phenoxy resin comprising 91.2 wt % polymer (PKCP-67) and 8.8 wt % paclitaxel (PTx).

DETAILED DESCRIPTION OF THE INVENTION

The present invention relates to radiation resistant polymers that are useful for the delivery of a therapeutic agent in connection with an intravascular or intervascular medical device.

According to an aspect of the present invention, a radiation-sterilized medical device is provided, which includes: (a) at least one release region that contains or consists essentially of a radiation resistant polymer and (b) at least one therapeutic agent. The radiation resistant polymer, in turn, contains or consists essentially of one or more phenoxy resin blocks (referred to below as a "phenoxy-resin-block-containing polymer").

Release regions for use in accordance with the present invention include carrier regions and barrier regions. By "carrier region" is meant a release region which further comprises a therapeutic agent and from which the therapeutic agent is released. For example, in some embodiments, a carrier region is disposed over all or a portion of a medical device substrate. In other embodiments, a carrier region constitutes the entirety of the medical device.

By "barrier region" is meant a region which is disposed between a source of therapeutic agent and a site of intended release, and which controls the rate at which therapeutic agent is released. For example, in some embodiments, the medical device is provided with a barrier region that surrounds a source of therapeutic agent. In other embodiments, a barrier region is disposed over a source of therapeutic agent, which is in turn disposed over all or a portion of a medical device substrate.

Hence, in various embodiments, release regions for use in accordance with the present invention are in the form of release layers, which cover all or a part of a medical device substrate. As used herein a "layer" of a given material is a region of that material whose thickness is small compared to both its length and width. As used herein a layer need not be planar or conformal (for example, taking on the contours of an underlying substrate). Layers can be discontinuous (e.g., patterned). Terms such as "film," "layer" and "coating" may be used interchangeably herein.

Medical devices for use in conjunction with the present invention include essentially any medical device for which controlled release of a therapeutic agent is desired. Examples of medical devices include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filter coils (including Guglilmi detachable coils and metal coils), vascular grafts, myocardial plugs, patches, pacemakers and pacemaker leads, heart valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and tissue engineering scaffolds for cartilage, bone, skin and other in vivo tissue regeneration.

The medical devices of the present invention include medical devices that are used for either systemic treatment or for the localized treatment of any mammalian tissue or organ. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, vagina, uterus, ovary, and prostate; skeletal muscle; smooth muscle; breast; dermal tissue; cartilage; and bone.

Specific examples of medical devices for use in conjunction with the present invention include vascular stents, which deliver therapeutic agent into the vasculature for the treatment of restenosis. In these embodiments, the release region is typically provided over all or a portion of a stent substrate, and is typically in the form of a carrier layer (in which case therapeutic agent is disposed within the release layer) or a barrier layer (in which case the release layer is disposed over a therapeutic-agent containing region).

As used herein, "treatment" refers to the prevention of a disease or condition, the reduction or elimination of symptoms associated with a disease or condition, or the substantial or complete elimination of a disease or condition. Preferred subjects are mammalian subjects and more preferably human subjects.

By "radiation sterilized" is meant that the medical device has been exposed to a quantity of radiation that is effective to kill pathogens associated with the medical device. The radiation that is used to sterilize the medical devices of the present invention is typically ionizing radiation, such as gamma radiation, X-ray radiation, or electron beam radiation. For example, sterilizing radiation doses for medical devices typically ranges between 100,000 rads and 100 Mrad. This includes, for example, 100,000 rads, 500,000 rads, 1,000,000 rads (1 Mrad), 2.5 Mrad, 5 Mrad, 7.5 Mrad, 10 Mrad, 20 Mrad, 50 Mrad and 100 Mrad, as well as ranges between any two of these doses, for example, 100,000 rad to 1 Mrad, 500,000 rad to 20 Mrad, and so forth, with 1 Mrad to 10 Mrad being a particularly beneficial range.

By "radiation resistant polymer" is meant that, at typical radiation sterilization doses employed as discussed above (e.g., 1 Mrad to 10 Mrad), the homopolymer or copolymer does not undergo significant changes in either molecular weight (e.g., Mw, Mn, via either crosslinking or chain scission) or morphology that significantly change a functional property of a device or coating (e.g., drug delivery properties or mechanical properties, such as elongation modulus, of a release region in accordance with the present invention) that negatively impacts its performance for its intended application.

As used herein, polymers are molecules containing one or more chains, which contain multiple copies of one or more constitutional units (commonly known as monomers), typically from 2 to 5 to 10 to 25 to 50 to 100 or even more constitutional units. As used herein, copolymers are polymers that contain at least two dissimilar constitutional units.

As used herein, a polymer "block" is a grouping of from 2 to 5 to 10 to 25 to 50 to 100 or more constitutional units. Blocks can be branched or unbranched. Blocks can contain a single type of constitutional unit (referred to herein as "homopolymeric blocks") or multiple types of constitutional units (referred to herein as "copolymeric blocks"). A "chain" is a linear (unbranched) grouping of 10 or more constitutional units (i.e., a linear block). Blocks and chains can correspond to entire polymers (e.g., to homopolymers, or random, statistical, gradient, or periodic copolymers, for instance, an alternating copolymer) or they can correspond to portions of copolymers, for example, to portions of block copolymers, graft copolymers and so forth. A "biodisintegrable polymer block" is a polymer block that undergoes dissolution, degradation, resorption and/or other disintegration process upon administration to a patient. The disintegration process may involve surface-erosion, bulk erosion or a combination of both.

A "phenoxy resin block" as used herein refers to a thermoplastic aromatic polyether block, typically one having a polymer backbone that contains aromatic moieties (e.g., phenylene containing moieties) linked by aliphatic ether linkages having pendant hydroxyl groups. They can be of high molecular weight (e.g., about 20,000 daltons or greater). Structurally, they are usually classified as polyols or polyhydroxy ethers. Polydispersity is typically less than about 4.0. An average phenoxy resin block typically contains forty or more regularly spaced hydroxyl groups. As discussed in further detail below, the term "phenoxy resin block" as used herein includes modified phenoxy resins, for example, but not limited to, modification by esterification of the secondary backbone hydroxyl groups to create pendant primary hydroxyl groups and water-borne phenoxy resin dispersions.

As indicated above a phenoxy resin block can correspond to an entire polymer, or it can correspond to only a portion of a polymer, for example, a copolymer containing a phenoxy resin block, such as a phenoxy resin block grafted with other polymer blocks such as an aliphatic polyester block. Polymers comprising phenoxy resin blocks can also be blended with other polymers.

As noted above, the medical devices of the present invention are radiation-sterilized, and contain (a) at least one release region that contains, or consists essentially of, a radiation resistant polymer and (b) at least one therapeutic agent. The radiation resistant polymer, in turn, contains, or consists essentially of, one or more phenoxy resin blocks.

Unmodified phenoxy resin blocks suitable for use in the radiation resistant polymers of the present invention include, for example, poly(hydroxy ether) blocks having terminal alpha-glycol groups. For example, the phenoxy resin blocks may contain one or more constitutional units represented by the following general formula (I):

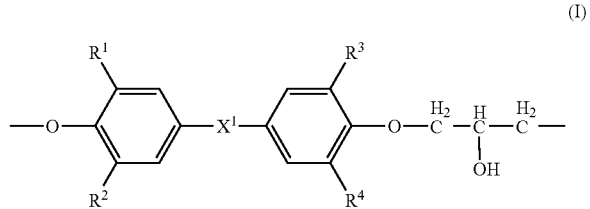

(I)

wherein, $X^1$ and $X^2$ each represent a divalent organic group or a bond. There are no particular limitations on the divalent organic group represented by $X^1$, which may include but is not limited to, for example: $-C(CH_3)_2-$, $-H_2-$, $-CH_3CH-$, $-O-$, $-CO-$, $-CH_2-CH_2-$, $-CH_3C(CH_2)CH(CH_3)_2-$, $-C(CF_3)_2-$, $-C(CH_3)CH(C_2H_5)((CH_2)_3(CH_3))-$, and $-Si(CH_3)_2-$. $R^1$, $R^2$, $R^3$, and $R^4$ are each independently selected from a hydrogen atom, an alkyl group having 1 to 4 carbon atoms (such as a methyl group, an ethyl group, a propyl group, a butyl group, an isopropyl group or an isobutyl group) and an electron-withdrawing group. $R^1$, $R^2$, $R^3$, and $R^4$ may be the same or different. An electron-withdrawing group, as used herein, refers to an atom or group having a (+) value, including halogen atoms such as fluorine atoms, a chlorine atom and a bromine atom, a trifluoromethyl group, a trichloromethyl group, a tribromomethyl group, a nitro group, a nitrile group, alkoxyl groups such as a methoxyl group and an ethoxyl group, a carboxyl group, alkylcarbonyl groups such as a methylcarbonyl group and an ethyl carbonyl group, alkoxycarbonyl group such as a methoxycarbonyl group and an ethoxycarbonyl group and alkylsulfoxyl groups.

The phenoxy resin blocks may be copolymer blocks composed of multiple constitutional units of the same or different type. For example, the copolymer block may be composed of two or more types of constitutional units wherein one or more of $X^1$, $R^1$, $R^2$, $R^3$, or $R^4$ is different among the units. When the phenoxy resin block contains constitutional units of two or more types, at least one unit may preferably be contained in the copolymer block.

Some preferred phenoxy resin blocks may comprise multiple units of one or both of the structures (II) and (III) as follows:

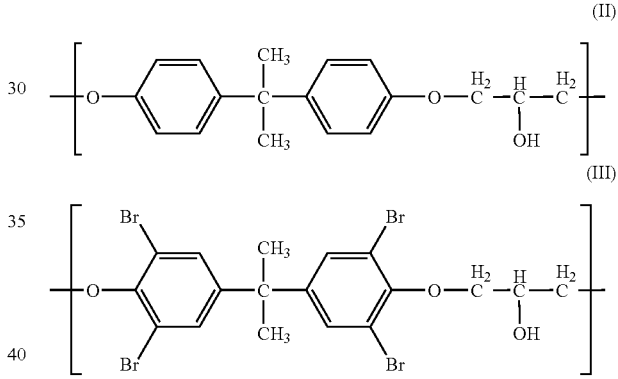

Many polymers containing the constitutional units represented by formula (I) are commercially available as standard solid grade pellets, powders, and solvent solutions (for example, PKHB, PKHC, PKHH, PKHJ, PKFE, PKHP, PKHB, and PKHS, all from InChem Corp., Rock Hill, S.C.).

In some other embodiments, the radiation resistant polymers of the present invention contain one or more modified phenoxy resin blocks. Examples include water-borne phenoxy resin dispersions (for example, PKHW-34, PKHW-35, and PKHW-36, commercially available from InChem Corp.), in which ethylenically unsaturated monomers such as acrylic acid, methacrylic acid, itaconic acid, maleic acid, fumaric acid and the like have been grafted onto the aliphatic carbon segments of the phenoxy resin backbone using standard polymerization techniques. Further details of the preparation of modified phenoxy resins of this type are provided in U.S. Pat. No. 6,034,160, the contents of which are hereby incorporated by reference in their entirety.

In certain preferred embodiments, the radiation resistant polymers of the present invention contain phenoxy resin blocks that have been modified to enhance certain mechanical and/or chemical properties such as to lower glass transition temperatures, increase compatibility with alkyl esters and polyesters and reactivity with cross-linkers like isocyanates, phenolic and melamine resins along the backbone hydroxyl groups. In some of these embodiments, the radiation resistant polymer is a graft copolymer comprising a phenoxy resin block as a main chain and a plurality of side chains. In some embodiments, the side chains of the graft copolymer comprise a polymer, including, but not limited to, polyesters, polyester urethanes, polyether urethanes, polyalkylene ethers, polyacrylates, polymethacrylates, polyarylates and polyolefins, among others.

The side chains of the graft copolymer may comprise, for example, a biodisintegrable polymer. Examples of some biodisintegrable side chains include the following: (a) polyesters, for example, homopolymers and copolymers of hydroxyacids and lactones, such as glycolic acid, lactic acid, tartronic acid, fumaric acid, hydroxybutyric acid, hydroxyvaleric acid, dioxanone, caprolactone and valerolactone, (b) polyanhydrides, for example, homopolymers and copolymers of various diacids such as sebacic acid and 1,6-bis(p-carboxyphoxy)alkanes, for instance, 1,6-bis(p-carboxyphoxy) hexane and 1,6-bis(p-carboxyphoxy)propane; (c) tyrosine-derived polycarbonates, (d) tyrosine-derived polyarylates and (e) polyorthoesters.

In particular embodiments, the side chains of the graft copolymer comprise a biodisintegrable material comprising a polyester. In some preferred embodiments, the side chains comprise an aliphatic polyester selected from the group consisting of homopolymers and copolymers of lactide, epsilon-caprolactone, glycolide, hydroxybutyrate, hydroxyvalerate, para-dioxanone, trim ethylene carbonate and its alkyl derivatives, 1,4-dioxepan-2-one, 1,5-dioxepan-2-one, and 6,6-dimethyl-1,4-dioxan-2-one.

The structure of an exemplary polymer comprising a phenoxy resin block modified with polycaprolactone side chains is represented below:

ing the concentration of pendant hydroxyl groups or varying the length of the pendant side chains (e.g., varying X). Referring to structure (IV), grafting of side chains comprising epsilon-caprolactone introduces primary hydroxyls into the polymer. In particular, as compared with the unmodified phenoxy resin with backbone hydroxyl groups, in the preferred embodiment represented by structure (IV), random secondary hydroxyls of the phenoxy resin have been converted into primary hydroxyls pendant on relatively short side chains compared to the longer phenoxy backbone. For random branches wherein x is typically less than about 3, the resulting modified resins have lower glass transition temperatures than unmodified phenoxy resin blocks. Phenoxy resin blocks having a α-caprolactone modification to the backbone as shown in structure (V) are commercially available (from InChem Corp., as PKCP-67 and PKCP-80). Many other polymers containing phenoxy resin blocks are commercially available, for example, YPB-43C, YPB-43D, and YPB-40AM40 (Tohto Kasei Co. Ltd.) for the devices of the present invention.

As will be appreciated by one of skill in the art, modified phenoxy resins can also be blended with unmodified phenoxy resin to obtain intermediate levels of reactivity with cross-linkers such as those discussed above, hardeners, and the like.

The phenoxy-resin-block-containing polymers for use in the release regions of the present invention may have, for example, a linear or branched configuration. Branched configurations include star-shaped configurations (e.g., configurations in which three or more chains emanate from a single branch point), comb configurations (e.g., configurations having a main chain and a plurality of side chains) and dendritic configurations (e.g., arborescent and hyperbranched polymers). The chain or chains forming the polymer may contain, for example, (a) a repeating series of constitutional units of a

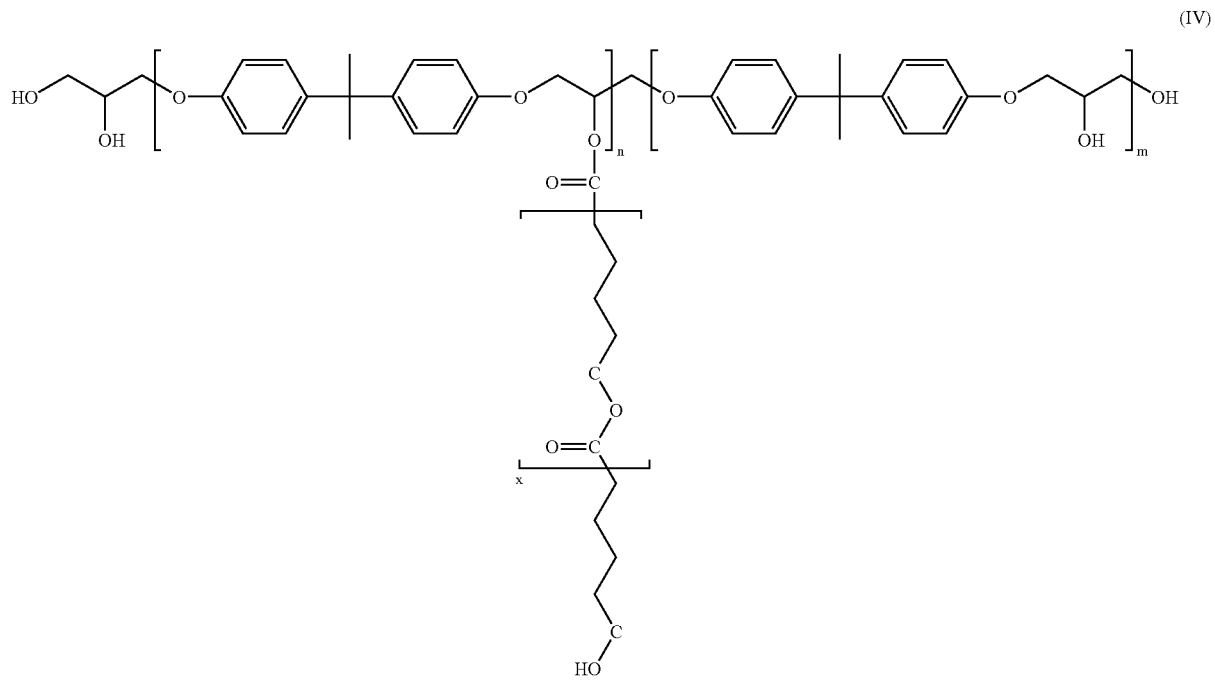

(IV)

wherein n+m is typically greater than about 40 and x is an integer greater than or equal to 2, typically 10 to 100, preferably 50-100 and in some embodiments, 2 to 10. Certain properties of the phenoxy resin block such as the glass transition temperature, may be modulated by, for example, varysingle type (e.g., constitutional units of formula (I) above), or (b) a series of constitutional units of two or more types, for instance, arranged in a repeating (e.g., alternating), random, statistical or gradient distribution. For example, the radiation resistant polymer of the present invention may comprise a phenoxy resin block comprising a random copolymer of the constitutional units of structures (II) and (III) above, or may comprise a random grafted copolymer like that of structure (IV), or may comprise one or more blocks of unmodified phenoxy resin along with one or more blocks of modified phenoxy resin such as α-caprolactone grafted phenoxy resin, and so forth.

A phenoxy-resin-block-containing polymer may be synthesized, for example, by allowing a bifunctional phenol to react with an epihalohydrin until the reaction product has a high molecular weight or subjecting a bifunctional epoxy resin and a bifunctional phenol to a polyaddition reaction. For example, a phenoxy resin can be obtained by allowing 1 mol of a bifunctional phenol to react with 0.985 mol to 1.015 mols of an epihalohydrin in the presence of an alkali metal hydroxide, in a non-reactive solvent and at a temperature of from 40 to 120° C. The epihalohydrin may include epichlorohydrin, epibromohydrin and epiiodohydrin. The bifunctional phenol may be any phenol including compounds having two phenolic hydroxyl groups, as exemplified by monocyclic bifunctional phenols such as hydroquinone, 2-bromohydroquinone, resorcinol and catechol; bisphenols such as bisphenol A, bisphenol F, bisphenol AD, and bisphenol S; dihydroxybiphenyls such as 4,4'-dihydroxybiphenyl; dihydroxyphenyl ethers such as bis(4-hydroxyphenyl)ether; any of these into the aromatic ring of the phenolic skeleton of which a straight-chain alkyl group, a branched alkyl group, an aryl group, a methylol group, an allyl group, a cyclic aliphatic group, a halogen (e.g., tetrabromobisphenol A) or a nitro group has been introduced, and polycyclic bifunctional phenols including those in which any of these into the carbon atom present at the center of the bisphenolic skeleton of which a straight-chain alkyl group, a branched alkyl group, an allyl group, a substituted allyl group, a cyclic aliphatic group or an alkoxycarbonyl group has been introduced.

In other embodiments, the release regions of the present invention comprise a blend of a phenoxy-resin-block-containing polymer and another supplemental polymer. A variety of polymers are available for use as supplemental polymers in the release regions of the present invention. For example, the supplemental polymer may be a homopolymer or a copolymer (including alternating, random, statistical, gradient and block copolymers), may be cyclic, linear or branched (e.g., polymers have star, comb or dendritic architecture), may be natural or synthetic, and may be thermoplastic or thermosetting.

Supplemental polymers for the practice of the invention may be selected, for example, from the following: polycarboxylic acid homopolymers and copolymers including polyacrylic acids; acetal homopolymers and copolymers; acrylate and methacrylate homopolymers and copolymers (e.g., n-butyl methacrylate); cellulosic homopolymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene homopolymers and copolymers; polyimide homopolymers and copolymers such as polyether block imides, polyamidimides, polyesterimides, and polyetherimides; polysulfone homopolymers and copolymers including polyarylsulfones and polyethersulfones; polyamide homopolymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); homopolymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic homopolymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide homopolymers and copolymers including polyethylene oxides (PEO); polyesters including polyethylene terephthalates and aliphatic polyesters such as homopolymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether homopolymers and copolymers including polyarylethers such as polyphenylene ethers, polyether ketones, polyether ether ketones; polyphenylene sulfides; polyisocyanates; polyolefin homopolymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated homopolymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone homopolymers and copolymers; polyurethanes; p-xylylene polymers; polyiminocarbonates; copoly (ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Particularly beneficial supplemental polymers include polyesters, polyester urethanes, polyether urethanes, and polyalkylene ethers. For example, the release region of the present invention can comprise a blend of a phenoxy-resin-block-containing polymer and a polyester, such as one selected from homopolymers and copolymers of lactide, epsilon-caprolactone, glycolide, hydroxybutyrate, hydroxyvalerate, para-dioxanone, trimethylene carbonate and its alkyl derivatives, 1,4-dioxepan-2-one, 1,5-dioxepan-2-one, and 6,6-dimethyl-1,4-dioxan-2-one. A copolymer blend of phenoxy resin and polyester (PKHM-301) is available from InChem Corp.

Numerous techniques are available for forming the release regions of the present invention. For example, where the selected phenoxy-resin-block-containing polymer (and supplemental polymer, if any) has thermoplastic characteristics, a variety of standard thermoplastic processing techniques can be used to form the release region, including compression molding, injection molding, blow molding, spinning, vacuum forming and calendaring, as well as extrusion into sheets, fibers, rods, tubes and other cross-sectional profiles of various lengths.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the phenoxy-resin-block-containing polymer prior to thermoplastic processing, producing a therapeutic-agent containing carrier region. If not, then a carrier region can nonetheless be formed by subsequent introduction of therapeutic agent, for example, as discussed below.

Release regions can also be formed using solvent-based techniques in which the phenoxy-resin-block-containing polymer (and supplemental polymer, if any) is first dissolved or dispersed in a solvent and the resulting mixture is subsequently used to form the release region.

Where solvent-based techniques are used, the solvent system that is selected will contain one or more solvent species. The solvent system preferably is a good solvent for the phenoxy-resin-block-containing polymer and, where included, for the supplemental polymer and therapeutic agent as well. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In many embodiments, a mixture containing solvent, phenoxy-resin-block-containing polymer and optional supplemental polymer and therapeutic agent, if any, is applied to a substrate to form a release region. For example, the substrate can be all or a portion of an implantable or insertable medical device, such as a stent, to which a release layer is applied. On the other hand, the substrate can also be, for example, a template from which the release region is removed after solvent elimination. Such template-based techniques are particularly appropriate for forming simple objects such as sheets, tubes, cylinders and so forth, which can be easily removed from a template substrate.

In other techniques, for example, fiber forming techniques, the release region is formed without the aid of a substrate or template.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be dissolved or dispersed in the polymer/solvent mixture if desired, and hence co-established with the carrier region. In other embodiments, on the other hand, the therapeutic agent can be dissolved or dispersed within a solvent, and the resulting solution contacted with a polymer region that is previously formed using, for example, one or more of the application techniques described above (e.g., dipping, spraying, etc.).

Barrier layers, on the other hand, are formed over a therapeutic-agent-containing region, for example, using solvent-based techniques such as those discussed above in which the phenoxy-resin-block-containing polymer and supplemental polymer, if any, are first dissolved or dispersed in a solvent, and the resulting mixture is subsequently used to form the barrier layer. The barrier layer serves, for example, as a boundary layer to retard diffusion of the therapeutic agent, for example, acting to prevent a burst phenomenon whereby much of the therapeutic agent is released immediately upon exposure of the device or a portion of the device to the implant or insertion site.

In some embodiments, the therapeutic-agent-containing region beneath the barrier region will comprise one or more polymers such as those described elsewhere herein. (In these embodiments, the polymeric composition of the barrier region may, or may not be the same as the polymeric composition of the underlying therapeutic-agent-containing region.) As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

Where the release region is formed using a solvent-based technique, it is preferably dried after application to remove the solvents. The release region typically further conforms to any underlying surface during the drying process.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (O) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomycin D, Resten-NG, Ap-17, abciximab, clopidogrel, ridogrel, beta-blockers, bARKct inhibitors, phospholamban inhibitors, and Serca 2 gene/protein, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences, such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/ Guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/ releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitrosocompounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and $\beta$-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (O) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t)

HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Therapeutic agents also include ablation agents, sufficient amounts of which will result in necrosis (death) of undesirable tissue, such as malignant tissue, prostatic tissue, and so forth. Examples include osmotic-stress-generating agents, for example, salts such as sodium chloride or potassium chloride; organic solvents, particularly those such as ethanol, which are toxic in high concentrations, while being well tolerated at lower concentrations; free-radical generating agents, for example, hydrogen peroxide, potassium peroxide or other agents that can form free radicals in tissue; basic agents such as sodium hydroxide; acidic agents such as acetic acid and formic acid; enzymes such as collagenase, hyaluronidase, pronase, and papain; oxidizing agents, such as sodium hypochlorite, hydrogen peroxide or potassium peroxide; tissue fixing agents, such as formaldehyde, acetaldehyde or glutaraldehyde; and naturally occurring coagulants, such as gengpin.

A wide range of therapeutic agent loadings can be used in connection with the medical devices of the present invention, with the pharmaceutically effective amount being readily determined by those of ordinary skill in the art and ultimately depending, for example, upon the condition to be treated, the nature of the therapeutic agent itself, the nature of the medical device, and so forth.

As will be appreciated by one of ordinary skill in the art, the release profile associated with the release region can be modified, for example, by altering the chemical composition of the release region (e.g., by changing the chemical composition of the phenoxy-resin-block-containing polymer, by blending one or more supplemental polymers with the phenoxy-resin-block-containing polymer, etc.) and/or by changing the physical structure of the release region or surrounding regions (e.g., by adding a separate barrier layer that contains one or more polymers, etc.).

The release profile associated with a release region of the medical device can also be modified by changing the number, order, thickness, or position of carrier and barrier regions with respect to one another. For example, the release profile can be modified by varying the thickness of the release region. Moreover, multiple release regions can be employed to modify the release profile, for example, (a) a barrier layer containing the phenoxy-resin-block-containing polymer of the invention can be positioned over a carrier layer containing the phenoxy-resin-block-containing polymer of the invention and a therapeutic agent, (b) multiple carrier layers of the invention, either of the same or different content (e.g., different polymer and/or therapeutic agent content) can be stacked on top of one another, either with or without intervening barrier layers, (c) multiple carrier layers of the invention of differing compositions can be positioned laterally with respect to one another, and so forth. In addition, where a carrier region is employed, a therapeutic-agent concentration gradient can be established within the carrier region to control release of therapeutic agent. For example, the therapeutic agent may be dispersed in a solution rather than solubilized by a solvent such that a concentration gradient of dispersed therapeutic agent particles is created in the carrier region.

EXAMPLE

Stent Coatings

1. Preparation of Coatings
   a. Paclitaxel
   A solution that contains 5 wt % tetrahydrofuran (THF), 94 wt % toluene, 0.088 wt % paclitaxel and 0.912 wt % polymer is prepared. The solution is prepared by mixing the polymer with the toluene and heating to 70° C. for about an hour, cooling to room temperature, adding the THF, adding the paclitaxel, thoroughly mixing (e.g., overnight), and filtering. The polymer in the solution comprises 0.912 wt % of a copolymer comprising caprolactone-modified phenoxy resin (PKCP-67, InChem Corp.). The solution (1) is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying such that the nozzle moves along the stent while spraying for one or more passes. After a carrier coating is formed in this fashion, the stent is dried, for example, by placing it in a preheated oven for 30 minutes at 65° C., followed by 3 hours at 70° C. Eight stents are formed in this manner for solution (1).

2. Drug Release from Stent Coatings
   The release of paclitaxel from stent coatings prepared according to the present invention is measured as a function of time. The results, presented as the cumulative release of the paclitaxel as a function of time in PBS with 0.5% wt % Tween® 20 (polyoxyethylene(20)sorbitan monolaurate) available from Sigma-Aldrich, for a coating formed using the solution (1) described above is graphically illustrated in FIGS. 1.

FIG. 1 graphically illustrates the kinetic drug release data for a coating comprising 91.2% PKCP-67 copolymer 8.8% paclitaxel where the copolymer comprises a phenoxy resin main chain having random grafts of epsilon-caprolactone side chains. As shown in FIG. 1, more than 25% of the paclitaxel load was released over the course of ten days.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A radiation stable medical device comprising (a) a release region and (b) a therapeutic agent, said release region comprising a block copolymer that comprises a modified phenoxy resin block and an unmodified phenoxy resin block, wherein said modified phenoxy resin block comprises a phenoxy resin block containing esterified backbone hydroxyl groups and said unmodified phenoxy resin block does not contain esterified backbone hydroxyl groups, and wherein said modified phenoxy resin block comprises polyester biodegradable side chains.

2. The device of claims 1, wherein said release region is a carrier region that comprises said therapeutic agent.

3. The device of claims 1, wherein said release region is a barrier region disposed over a therapeutic-agent-containing region that comprises said therapeutic agent.

4. The device of claims 1, wherein said release region is in the form of a coating layer that covers all or a part of said medical device.

5. The device of claims 1, wherein at least a portion of said medical device is adapted for implantation or insertion into a subject.

6. The device of claims 1, wherein said medical device is selected from a catheter, a guide wire, a balloon, a filter, a stent, a stent graft, a vascular graft, a vascular patch and a shunt.

7. The device of claims 1, wherein said implantable or insertable medical device is adapted for implantation or insertion into the coronary vasculature, peripheral vascular system, esophagus, trachea, colon, biliary tract, urinary tract, prostate or brain.

8. The device of claims 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

9. The device of claim 1, wherein said medical device comprises a plurality of release regions.

10. The device of claim 1, wherein said medical device comprises a plurality of different therapeutic agents.

11. The device of claim 1, wherein said medical device comprises a plurality of different radiation resistant polymers.

12. The device of claim 1, wherein said block copolymer comprises at least one constitutional unit of the formula

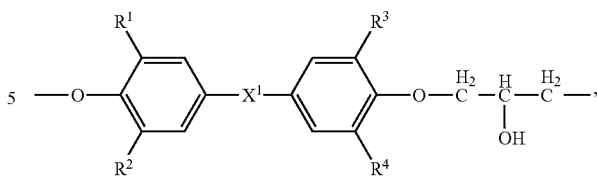

wherein $X^1$ represents a divalent organic group, and $R^1$, $R^2$, $R^3$, and $R^4$ are each independently selected from a hydrogen atom, an alkyl group having 1 to 4 carbon atoms, and an electron-withdrawing group selected from halogen atoms, trihalomethyl groups, a nitro group, a nitrile group, alkoxyl groups having 1 to 4 carbon atoms, a carboxyl group, alkylcarbonyl groups having 1 to 5 carbon atoms, alkoxycarbonyl group having 1 to 5 carbon atoms, alkylcarbonyloxy groups having 1 to 5 carbon atoms, and alkylsulfoxyl groups having 1 to 5 carbon atoms.

13. The device of claim 1, wherein said block copolymer comprises at least one constitutional unit of the formula

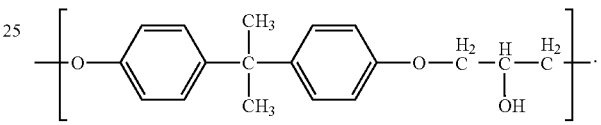

14. The device of claim 1, wherein said release region is radiation sterilized with a radiation dosage ranging from about 1 to about 10 Mrad.

15. The device of claim 1, wherein the block copolymer further comprises a biodisintegrable polymer block.

16. The device of claim 1, wherein the release region does not comprise a supplemental polymer.

17. The device of claim 1, wherein the release region does not comprise a supplemental polymer selected from vinyl aromatic homopolymers and copolymers.

18. The device of claim 1, wherein the polyester biodegradable side chains are selected from homopolymers and copolymers of hydroxyacids and lactones.

19. The device of claim 16, wherein the polyester biodegradable side chains are selected from homopolymers and copolymers of hydroxyacids and lactones.

20. A radiation stable medical device comprising (a) a release region and (b) a therapeutic agent, said release region comprising a block copolymer that comprises a modified phenoxy resin block and an unmodified phenoxy resin block, wherein said modified phenoxy resin block comprises a phenoxy resin block containing esterified backbone hydroxyl groups and said unmodified phenoxy resin block does not contain esterified backbone hydroxyl groups, wherein said modified phenoxy resin block comprises polycaprolactone side chains, and wherein said release region is radiation sterilized with a radiation dosage ranging from about 1 to about 10 Mrad.

* * * * *

UNITED STATES PATENT AND TRADEMARK OFFICE
CERTIFICATE OF CORRECTION

| | | |
|---|---|---|
| PATENT NO. | : 8,722,074 B2 | Page 1 of 1 |
| APPLICATION NO. | : 11/184196 | |
| DATED | : May 13, 2014 | |
| INVENTOR(S) | : Zhong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2102 days.

Signed and Sealed this
Twenty-first Day of July, 2015

Michelle K. Lee
*Director of the United States Patent and Trademark Office*